US00PP09233P

United States Patent [19]

Meilland

[11] Patent Number: Plant 9,233

[45] Date of Patent: Aug. 8, 1995

[54] SHRUB CLIMBING ROSE PLANT NAMED 'MEITOSIER'

[75] Inventor: Alain A. Meilland, Antibes, France

[73] Assignee: The Conard-Pyle Company, West Grove, Pa.

[21] Appl. No.: 314,389

[22] Filed: Sep. 28, 1994

[51] Int. Cl.[6] ..... A01H 5/00
[52] U.S. Cl. ..... Plt./4
[58] Field of Search ..... Plt. 1, 2, 3, 4

*Primary Examiner*—Howard J. Locker

*Attorney, Agent, or Firm*—Burns, Doane, Swecker & Mathis

[57] ABSTRACT

A new and distinct variety of Shrub Climbing rose plant is provided which forms attractive large lightly-fragrant light Mandarin Orange blossoms generally having the configuration of old roses. The blossoming is abundant and the plant reflowers well. The vegetation is vigorous and the plant possesses a climbing growth habit. The plant exhibits very good disease resistance particularly with respect to Marssonina and Black Spot.

1 Drawing Sheet

SUMMARY OF THE INVENTION

The new variety of Shrub Climbing rose plant of the present invention was created by artificial pollination wherein two parents were crossed which previously had been studied in the hope that they would contribute the desired characteristics. The female parent (i.e., the seed parent) was the product of the pollination of the Meipalsar variety (non-patented in the United States) and the Golden Showers variety (U.S. Plant Pat. No. 1,557). The male parent (i.e., the pollen parent) of the new variety was the Light Konigin Lucia variety (non-patented in the United States). The parentage of the new variety can be summarized as follows:

(Meipalsar × Golden Showers) × Licht Konigin Lucia.

The seeds resulting from the above pollination were sown and 116 small plants were obtained which were physically and biologically different from each other. Selective study resulted in the identification of a single plant of the new variety.

It is found that the new variety of Shrub Climbing rose plant possesses the following combination of characteristics:

(a) forms attractive large lightly-fragrant light Mandarin Orange blossoms having an old-rose configuration,
(b) exhibits a propensity for climbing,
(c) exhibits a good ability to reflower, and
(d) is particularly suited for growing as ornamentation in the landscape.

The new variety meets the needs of the horticultural industry. It can be grown to particular advantage as attractive ornamentation in parks, gardens, public areas, and residential landscapes.

The characteristics of the new variety have been found to be homogeneous and stable and are strictly transmissible by asexual propagation carried out in France (e.g., by budding, grafting, and cuttage) from one generation to another.

The new variety has been named the Meitosier variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were three years of age and were observed during September while budded on *Rosa froebelii* understock and growing outdoors at Le Cannet des Maures, Var, France.

DETAILED DESCRIPTION

Figures 1, 2, 3, 4, 5, 6, 7, 8, 9, 10, 11, 12, 13, 14, 15, 16:
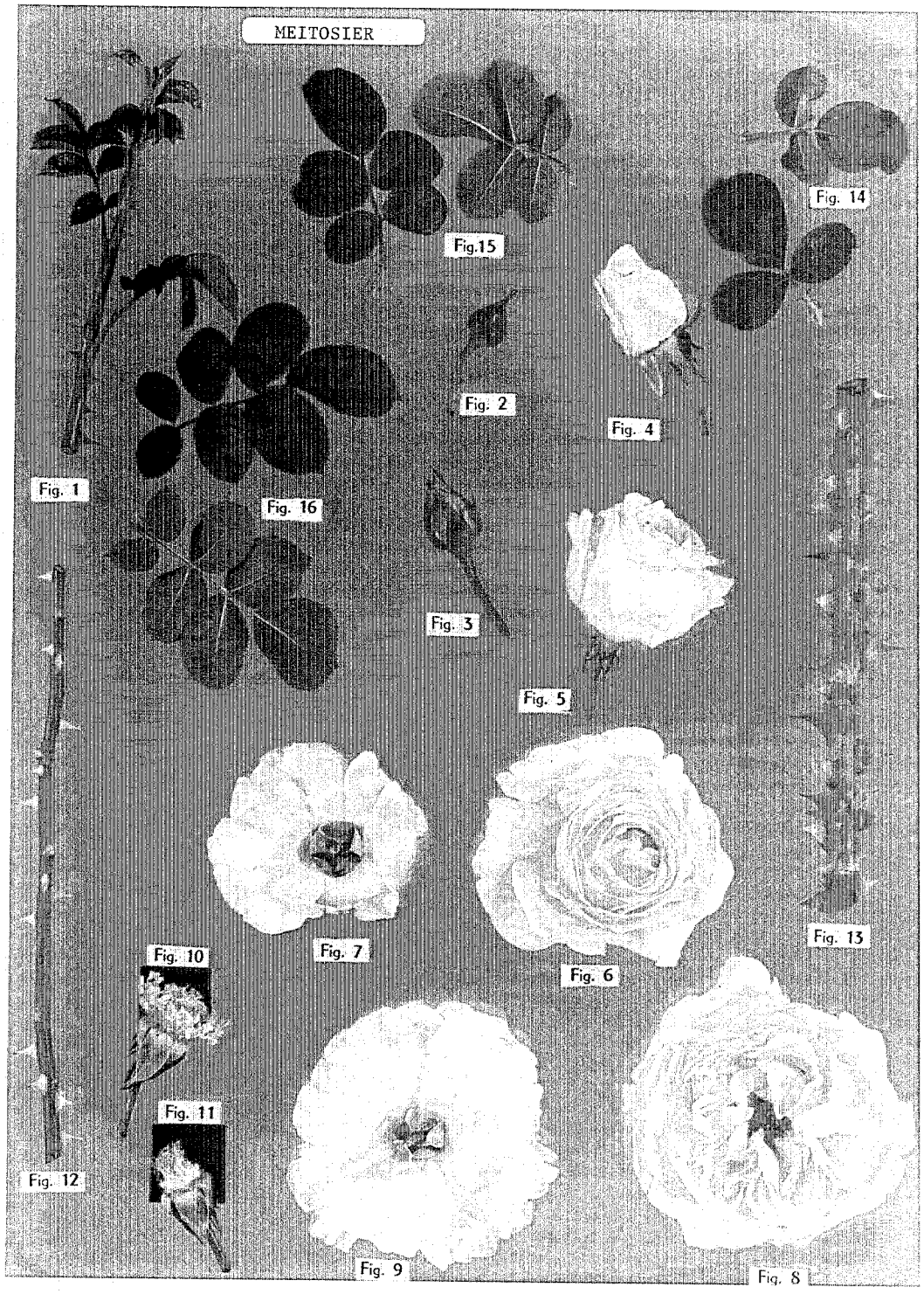
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower in the course of blooming.
FIG. 6 illustrates a specimen of a open flower — plan view — obverse.
FIG. 7 illustrates a specimen of a open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a floral stem.
FIG. 13 illustrates a specimen of a main branch.
FIG. 14 illustrates specimens of leaves with three leaflets — upper (at bottom) and under (at top) surfaces.
FIG. 15 illustrates specimens of leaves with five leaflets — upper (at left) and under (at right) surfaces.
FIG. 16 illustrates specimens of leaves with seven leaflets — plan view — upper (at top) and under (at bottom) surfaces.

The chart used in the identification of the colors is that of The Royal Horticultural Society (R.H.S. Colour Chart). The terminology preceding the numbered reference to the chart has been added to indicate the corresponding color in more common terms. The description is based on the observation of three year-old specimens of the new variety during June while growing outdoors when budded on *Rosa froebelii* understock at Le Cannet des Maures, Var, France.

Class: Shrub climbing.

Plant:

*Height.*—Approximately 150 to 200 cm. on average at the end of the growing season.

*Habit.*—Climbing.

Branches:

*Color.*—Young stems: lettuce green, Yellow-Green Group 144B. Adult wood: medium green, Yellow-Green Group 146B.

*Thorns.*—Size: medium to small. Quantity: few on young stems and numerous on adult wood. Color: greenish on young stems and tan on adult wood as illustrated.

Leaves:

*Stipules.*—Adnate, pectinate, wide and linear.

*Petioles.*—Upper surface: striped reddish on young foliage and medium green on adult foliage with more or less glandular edges. Under surface: light green and smooth.

*Leaflets.*—Number: 3, 5 (most often), and 7. Shape: rounded. Serration: regular, as illustrated. Texture: very leathery. General appearance: dense and semi-glossy foliage. Color (young foliage): Upper surface: medium green, Green Group 137A. Under surface: light green, Green Group 137C. Color (adult foliage): Upper surface: dark green, Green Group 139A. Under surface: light green, Green Group 137C.

Inflorescence:

*Number of flowers.*—Usually one flower per stem.

*Peduncle.*—Light green with pediculate glands and approximately 3 to 4 cm. in length on average.

*Sepals.*—Upper surface: tomentose, and greenish in coloration. Under surface: light green with somewhat appendiculated and glandular edge.

*Buds.*—Shape: ovoid. Length: approximately 3 cm. on average. Size: large. Color when opening: Upper surface: light Indian Yellow, Yellow-Orange Group 17C, and widely suffused with Mandarin Orange, Orange Group 24C, becoming lighter on outer petals. Under surface: light Indian Yellow, Yellow-Orange Group 17D, and more or less suffused with Mandarin Orange, Orange Group 24C.

*Flower.*—Form: quartered shape like old rose. Diameter: approximately 9 to 10 cm. on average. Color (when opening begins): Upper surface: light Indian Yellow, Yellow-Orange Group 17D, and widely suffused with Mandarin Orange, Orange Group 24C, becoming lighter toward the edges of the petals. Under surface: light Indian Yellow, Yellow-Orange Group 17D, and widely suffused with Mandarin Orange, Orange Group 24C, becoming lighter toward the edges of the petals. Color (when blooming): Upper surface: light Mandarin Orange, Orange Group 24C, and light Indian Yellow, Yellow-Orange Group 17C toward the base. Under surface: light Mandarin Orange, Orange Group 24C, and light Indian Yellow, Yellow-Orange Group 17C toward the base. Color (at end of opening): Upper surface: light Mandarin Orange, Orange Group 24C, and light Indian Yellow, Yellow-Orange Group 17C toward the base. Under surface: light Mandarin Orange, Orange Group 24C, and light Indian Yellow, Yellow-Orange Group 17C toward the base. Fragrance: light. Lasting quality: long. Petal shape: outer petals are rounded with cuneate base and the inner petals are rounded with cordiform base. Petal number: approximately 90 to 100 on average. Petal drop: good. Stamen number: approximately 120 on average. Anthers: yellow-orange in coloration. Filaments: normal light fuchsine. Pistils: approximately 178 on average. Stigmas: normal, strawlike, and sometimes a vegetative center is developed. Styles: fuchsine in coloration, tomentose at base, and of irregular height. Receptacle: light green, smooth, and in longitudinal section in the shape of a funnel.

Development:

*Vegetation.*—Vigorous.

*Blooming.*—Abundant with good reflowering ability.

*Aptitude-to bear fruits.*—Poor.

*Resistance to distances.*—Very good particularly with respect to Marssonina and Black Spot.

I claim:

1. A new and distinct variety of Shrub Climbing rose plant characterized by the following combination of characteristics:

(a) forms attractive large lightly-fragrant light Mandarin Orange blossoms having an old-rose configuration, (b) exhibits a propensity for climbing, (c) exhibits a good ability to reflower, and (d) is particularly well-suited for growing as ornamentation in the landscape;

substantially as herein shown and described.

* * * * *

MEITOSIER